United States Patent [19]

Jansen et al.

[11] 4,376,867

[45] Mar. 15, 1983

[54] CHEMICAL PROCESS

[76] Inventors: Gert Jansen, Bastholmen 16, DK-3520 Farum; Per Wolff, 15A, DK-3460 Birkeroed, both of Denmark

[21] Appl. No.: 280,965

[22] Filed: Jul. 7, 1981

[51] Int. Cl.$^3$ .............................................. C07C 51/15
[52] U.S. Cl. ................................................... 562/424
[58] Field of Search ......................................... 562/424

[56] References Cited

U.S. PATENT DOCUMENTS 3,435,068   3/1969   Gehring et al. ..................... 562/424

FOREIGN PATENT DOCUMENTS 50-9789   4/1975   Japan .................................. 562/424

OTHER PUBLICATIONS

B.I.O.S. Final Report No. 664, Hem No. 22 (1946).

*Primary Examiner*—A. Siegel
*Attorney, Agent, or Firm*—Lawrence Rosen

[57] ABSTRACT

An improved process for the production of sodium salicylate and salicylic acid from phenol at a high degree of conversion with a concomitant reduction in undesirable by-products. The process comprises reacting a sodium phenolate with carbon dioxide in a direct, single step at a temperature above about 165° C. to produce directly sodium salicylate, which is then converted by conventional means to the salicylic acid.

6 Claims, No Drawings

CHEMICAL PROCESS

BACKGROUND OF THE INVENTION

The Kolbe-Schmitt reaction is a well known commercial route for the synthesis of salicylic acid. Lindsey and Jeskey have described the Kolbe-Schmitt synthesis as well as the present day industrial process in *Chemical Review*, Vol. 57, pp 584–591 (August, 1957). Other detailed descriptions are found in *Thorpe's Dictionary of Applied Chemistry*, 4th Edition, Volume 10, pp 660–665 (1950); and in *Kirk-Othmer Encyclopedia of Chemical Technology*, Second Edition, Volume 17, pp 724–727 (1968); and Hardy's article "Salicylic Acid" in *Industrial Eng. Chemistry*, Volume 69, pp 55A–56A (1957).

Improvements in the synthesis have been developed, and in the past these efforts have been mainly concerned with increasing the yields of salicylic acid by higher conversions of the phenol fed to reactor. These improvements have led to the commercial processes now in general use.

In these processes the carbon dioxide is introduced at temperatures below about 140° C., preferably between 100°–125° C., and only after the equimolar amount of carbon dioxide has been absorbed at this low temperature, is the temperature gradually riased to above 140°–150° C., typically to 150°–160° C. to effect the rearrangement of the sodium phenylcarbonate into the desired sodium salicylate. Any unreacted phenol is stripped from the reactor in vacuum and recovered for recycling. By the present day commercial processes the amount of phenol, which has to be removed at the end of the cycle, can be kept low, generally around 10–15% of the phenol initially charged to the reactor or autoclave.

The crude sodium salicylate product is dissolved in water and treated with activated carbon to remove color. Acidification with strong mineral acid precipitates the salicylic acid, which is then recovered by, for example, centrifugation. In general, mineral acids such as sulfuric and hydrochloric are employed for this purpose. The salicylic acid thus produced is of good quality generally containing about 99.5% salicylic acid. The main impurity being 4-hydroxybenzoic acid and 4-hydroxy-isophthalic acid. Whereas the established commercial processes give a relative high degree of conversion of the phenol charged and also give an acceptable purity of the end product, they are also characterized by an unrecoverable loss of phenol and a partly recoverable loss of product, which with rising costs of raw materials and energy becomes intolerable.

Although the end product, the commercial salicylic acid, may contain 99.5% salicylic acid and only about 0.5% by-products, the sodium salicylate only constitutes about 90–95% of the sodium salts of organic acids present in the crude carboxylation reaction products. The remainder being salts of 4-hydroxybenzoic acid (4-HBA), 2-hydroxy-isophthalic acid (2-HIPA), and 4-hydroxy-isophthalic acid (4-HIPA).

The known carboxylation conditions will typically produce the various acids in the following amounts:

|  | Mole % |
|---|---|
| Salicylic Acid | 90–95 |
| 4-HBA | 5–10 |
| 2-HIPA | 0.1–0.5 |
| 4-HIPA | 0.5–2 |

The by-product acids, especially 4-HBA, are much more soluble in water than salicylic acid itself, and thus they are easily separated from the salicylic acid by precipitating the salicylic acid from a dilute solution at an elevated temperature. This has in the past often led manufacturers to the conclusion that salicylic acid was the sole product of the carboxylation. A typical operation would be to dilute the crude salts to about 1 ton sodium salicylate in 8 to 10 tons of water and precipitate the salicylic acid by adding sulfuric acid at 50°–60° C. This would give a salicylic acid of 99.5% purity in a yield of about 85% of the salicylic acid present. A second impure product could be isolated by cooling the mother liquid to about 25° C., and by recycling this product for purification the total yield could be raised to about 95% of salicylic acid present. But generally an amount of salicylic acid equal to the amount of by-product acids produced will be lost with the mother liquid. In principle the acids could be recovered from the mother liquid by extraction with a solvent followed by evaporation of the solvent. Apart from adding to the capital cost and energy consumption, such additional process steps would only produce a 50:50 mixture of salicylic acid and by-product acids of little, if any, commercial value.

The hydroxy isophthalic acids are not so easily removed during the isolation of the salicylic acid. To produce a high purity salicylic acid the technical product is sublimated leaving the hydroxy isophthalic acids behind in the residue. Many of the problems caused by side reactions as well as the formation of undesirable by-products are discussed by G. A. Korzenovskii, *J. Chem. Ind.*, (USSR), Volume 2, pp 541-2 (1929), which is abstracted in *Chemical Abstracts*, Volume 24, 838[5].

It follows therefore that it would be desirable to have a process in which the amount of non-salicylic acids formed during the carboxylation step would be significantly reduced.

BRIEF DESCRIPTION OF THE INVENTION

In accordance with the present invention it now has been found surprisingly that in the Kolbe-Schmitt carboxylation the reaction between sodium phenolate and carbon dioxide could advantageously take place in one step well above the temperature at which sodium phenylcarbonate is ordinarily converted to sodium salicylate. More particularly, instead of introducing the stoichiometric amount of carbon dioxide below about 150° C. to produce sodium phenylcarbonate, which then, in a second step, is converted to sodium salicylate by being held above 150° C. for a considerable period of time, the carbon dioxide is reacted with sodium phenolate in a single step at a temperature above about 165° C. to produce sodium salicylate directly.

By practicing the process of this invention it is possible to reduce the amount of by-product non-salicylic acids and then sodium salts by a factor of 5 to 10 while maintaining a high degree of conversion of the phenol charged to the autoclave or reactor.

DETAILED DESCRIPTION OF THE INVENTION

In the process of this invention phenol and an aqueous sodium hydroxide solution are fed to a reaction zone. Water is removed as the temperature is raised to above 165° C. and carbon dioxide introduced while the reaction mixture is maintained under elevated temperatures and pressures to reduce sodium salicylate as the reaction product.

The molar ratio of phenol to sodium hydroxide will generally be about 1 to 1, and preferably only a small excess of phenol such as about 1 to 10% is utilized. Although somewhat larger amounts of phenol can be used in the present process, it is necessary to stay below about 25% excess phenol since too much phenol will lead to formation of lumps which in turn will cause mechanical problems in the processing equipment. Thus, for example, the use of a high ratio of phenol to sodium hydroxide, i.e., 4 to 1, as employed in the process disclosed in U.K. Pat. No. 949,988, where the reaction takes place in molten phenol, will give a complicated process and will not give any advantage with respect to formation of undesirable by-products.

The sodium hydroxide solution will generally be utilized as aqueous solutions having concentrations ranging from about 25 to 55% sodium hydroxide. Removal of water is then accomplished by heating the reaction mixture initially at ambient pressures and then under reduced pressures, e.g. from about 5 to 100 mm. at temperatures above about 165° C.

After water removal is substantially complete and after the phenol has been converted to sodium phenate, stoichiometric amounts of carbon dioxide are fed to reaction zone while the temperature is maintained above 165° C. Absorption of the carbon dioxide occurs immediately even though reduced pressures of from about 10 to 200 mm. exist in the reaction zone during the first part of the carboxylation. As the reaction proceeds, the pressure increased rapidly to about 4 to 6 bars and is maintained at this level for a period of time sufficient to complete the carboxylation, generally from about 0.5 to 4 hours. The time period of the initial carboxylation reaction will, of course, vary depending upon the operating conditions, the type of reactor or autoclave employed, etc. For most purposes, however, the initial time period may range from about 0.5 to 5 hours.

The sodium salicylate is recovered from the reaction zone by cooling the autoclave or reactor to temperatures of about 120° C. or lower. The reaction zone is then filled with water to obtain a concentrated stock solution of sodium salicylate. It will be understood that various known methods may be employed for the recovery of sodium salicylate and the exact method of recovery does not constitute an essential feature of the present invention. Furthermore, conventional procedures may be employed to convert the sodium salicylate to salicylic acid and then, if desired, to acetylsalicylic acid. See, for example, Thorpe or Kirk-Othmer, supra.

It should be noted, however, that due to the very small amount of by-products formed during the carboxylation according to the present invention, the recovery of salicylic acid is much simplified. More concentrated solutions can be employed during the precipitation of the salicylic acid, leading to higher capacity of the given process equipment and reduction in process water which has to be disposed of, and additional purification by dry sublimation is not required to obtain salicylic acid of the highest purity from the carboxylation product obtained from the process of the present invention.

It is not known whether sodium phenylcarbonate is formed as a precursor at the high carboxylation temperatures employed in the present carboxylation step. What is clear, however, is that there is no need for carrying out the carboxylation in two distinct steps: one, the reaction at about 100° C. between the sodium phenolate with carbon dioxide to form sodium phenylcarbonate; and, two, the conversion of the sodium phenylcarbonate with additional carbon dioxide to sodium salicylate utilizing reaction temperatures in the order of 140°–150° C.

In general, the carboxylation step of the present invention is carried out in one step at a temperature above about 165° C., preferably above about 175° C., and most preferably between about 180°–220° C. Higher temperatures, e.g. about 230° C., can also be effectively utilized, but then the pressure of the carbon dioxide should be increased from about 5 bars to about 8 to 10 bars during the latter part of the carboxylation reaction.

In contrast to published information, it has been found that the degree of conversion of sodium phenolate to sodium salicylate is practically independent of the reaction temperature. At 165° C. and at 200° C., 85–88% conversion is easily obtained, but by-product formation is reduced as the temperature is increased. For instance, reaction at 140°–150° C. gives about 9% non-salicylic acids mostly 4-HBA in the crude product mixture whereas reaction at 190°–195° C. (at 5 bar co-pressure) gives less than 0.5% non-salicylic acids in the reaction product mixture.

The reaction according to the basic invention may be conducted in any type of autoclave presently known to be suitable for the production of sodium salicylate. In accordance with another feature of this invention, the reaction is advantageously carried out in a kneader and mixing device according to U.S. Pat. No. 3,880,407 (Heinz List). Although this machine is intended for handling sticky, highly viscous materials such as molten polymers and gums, it has been found that surprisingly good results are obtained by conducting the reaction between sodium phenolate and carbon dioxide in said apparatus. Most unexpectedly it was found that the carbon dioxide can be introduced at a very high rate without adversely affecting yield or purity of sodium salicylate. This means that the stoichiometric amount of carbon dioxide can be introduced and reacted in a shorter period of time such as 1 to 6 hours instead of the usual 10 to 24 hours. This is clearly of great importance in commercial operations.

The mixer and kneader apparatus of U.S. Pat. No. 3,880,407 uses counteracting blades to ensure a satisfactory exchange of reactants takes place in carrying out the process of the present invention. The mixer and kneader is formed of a rotatable agitator mounted within a stationary, cylindrically shaped housing. In a number of axially spaced radially extending planes within the housing, a plurality of plate-like elements are secured to the agitator and extend outwardly to a point closely spaced from the inner surface of the housing. A stirrer blade is fixed to the radially outer edge of each of the plate-like elements and the blade extends in the axial direction. Positioned between each pair of adjacent planes of plate-like elements is a stationary counter element secured to the housing by means of a support mounting with a counter blade attached to the mounting at the point spaced inwardly from the inner surface of the housing. The counter blade extends in the axial direction in generally the same manner as the stirrer blades. The stirrer blades, during rotation, pass between the counter blades and the inner surface of the housing and afford a scraping or cleaning effect on the housing wall and, in combination with the counter blades, a kneading effect on the material within the housing. Similarly, the counter blades provide a cleaning or scraping effect on the surface of the agitator and also on the axially facing surfaces of the plate-like elements.

In addition to the foregoing description, the drawings and the disclosure in column 2, line 22, to column 6, line 10, of the Heinz List U.S. Pat. No. 3,880,407 is incorporated herein by reference.

The invention will be more fully understood by reference to the following comparative examples and illustrative examples of the present process:

COMPARATIVE EXAMPLES

Run A

In this run sodium salicylate was prepared in a conventional manner. 23.2 moles phenol and 22.9 moles sodium hydroxide were charged to an autoclave with a stirrer and dried, first at ambient pressure at 120°–125° C., and then under a vacuum of 23 mm hg at 140°–150° C. Total drying time was approximately 5 hours.

The sodium phenolate thus formed was cooled to 90° C. and carbon dioxide was passed into the autoclave. An exothermic reaction took place, and the temperature was maintained at about 120° C. until the carbon dioxide absorption came to an end. The temperature was then raised to induce rearrangement of the intermediate or precursor product. A slight additional consumption took place at about 145°–155° C. The temperature was kept at 160°–170° C. under a carbon dioxide pressure of 5 bars for 4 hours, whereupon the autoclave was cooled and the product sampled for analysis.

Run B

In this run the introduction of carbon dioxide took place at 120°–135° C.

A small sample of the crude sodium salicylate obtained in both Runs A and B was taken up in dilute hydrochloric acid to convert the salts to free acids. The solution was analyzed by high pressure liquid chromatography and gave the following composition in weight percent:

|  | Runs | |
| --- | --- | --- |
|  | A | B |
| 2-Hydroxy-isophthalic acid (2-HIPA) | 1.1 | 2.8 |
| 4-Hydroxybenzoic acid | 9.3 | 10.1 |
| The by-product acids thus constitute a direct loss of about 10–13% phenol. | | |

During the preparation of the pure salicylic acid the by-product acids are removed by precipitating the salicylic acid from a solution of the salts. The solution is kept so weak that the by-product acids remain in solution.

The work-up of the above products to give a 99.5% pure salicylic acid thus gives rise to an additional 10% loss of salicylic acid which either goes with the waste liquid or can only be isolated as a 50:50% mixture with the by-product acids.

Run C

The process described in U.K. Pat. No. 949,988 (Dow Chemical Co.) was repeated in a 7 liter autoclave with high shear agitation. The charge comprised 8 moles sodium phenolate dissolved in 30 moles phenol. Carbon dioxide was introduced at a temperature of 160°–165° C. and at a pressure of 5 bars for 2 hours.

The solid product was sampled from the autoclave and found to contain 5.5 mole % 4-HBA and 0.64% 4-HIPA, based on the total amount of mixed acids.

EXAMPLES OF THE INVENTION

EXAMPLE I

In a mixer and kneader apparatus described in U.S. Pat. No. 3,880,407 there was charged phenol 23.2 moles and sodium hydroxide 23.0 moles (as a 40% solution). The water was removed by heating first at ambient pressure and then at 30 mm Hg at a final temperature of 190° C. Carbon dioxide was then introduced at the rate of 5 moles per hour. Absorption was immediate and subatmospheric pressure existed in the autoclave for the first half of the carboxylation. At the end of 5 hours, however, the pressure increased rapidly to 5 bars and was maintained at this level for an additional 1 hour. The autoclave was cooled to 100° C. and filled with water to produce a concentrated stock solution of sodium salicylate.

Approximately 1% of the stock solution was diluted with 250 ml of deionized water. From this solution was taken 25 microliters and diluted with 5.0 ml of acidic diluent to convert the salts to the free acids. This sample was run on a high pressure liquid chromatograph and gave the following composition:

|  | Moles | Mole %, on Salicylic Acid |
| --- | --- | --- |
| Salicylic acid | 20.4 | — |
| 4-Hydroxy-isophthalic acid (4-HIPA) | 0.026 | 0.13 |
| 4-Hydroxybenzoic acid (4-HBA) | 0.054 | 0.27 |
| Phenol | 1.42 | — |

The yield of salicylic acid based on phenol charged, is thus 88%. Since any unreacted phenol can be completely recycled the real loss in the process is the sum of 4-HIPA and 4-HBA, or a total of 0.4 mole %.

EXAMPLE 2

Example 1 was repeated except for using a carbon dioxide flow of 20 moles per hour. Analysis gave the following composition of the acids formed:

|  | Mole % |
| --- | --- |
| Salicylic acid | 99.52 |
| 4-HBA | 0.35 |
| 4-HIPA | 0.19 |

EXAMPLE 3

The experiments of Example 1 and 2 were repeated using the other temperatures during the carboxylation. The products were analyzed as described in Example 1, and the following results were obtained:

TABLE

| Run No. | °C.[a] | Mol/Hr[b] | Mol %[c] | By-Products, Mole %[d] | |
|---|---|---|---|---|---|
| | | | | 4-HBA | 4-HIPA |
| 3-1 | 160–166 | 5 | 85 | 4.1 | 0.4 |
| 3-2 | 173–179 | 5 | 93 | 1.3 | 0.26 |
| 3-3 | 177–184 | 5 | 85 | 1.4 | 0.27 |
| 3-4 | 192–204 | 20 | 87 | 0.35 | 0.12 |
| 3-5 | 190–195 | 5 | 60 (2) | 0.26 | 1.0 |
| 3-6 | 140–157 | 20 | 87 | 8.2 | 0.76 |
| 3-7 | 237–243 | 5 | 31 (3) | 1.8 | 0.11 |

[a] temperature during introduction of carbon dioxide
[b] $CO_2$ flow, moles/hr
[c] conversion of phenol, mole %
[d] amount of by-product acids in mole % of salicylic acid formed.

The data in above Table show the benefit of introducing the carbon dioxide and carrying out the carboxylation at elevated temperatures, i.e. preferably above about 165° C. and most preferably between about 180° to 220° C.

Runs 3-5 show the effect of incomplete drying of the sodium phenolate. The conversion is reduced, but the formation of by-products is not influenced. Similarly Run 3-7 shows that at very high temperatures the conversion is also limited due to the high partial vapour pressure of the phenol at these temperatures.

A summary of the results of Table 3 will show a minimum in the formation of 4-HBA around 180°–210° C. and these, and other Runs, show that in order to keep the formation of 4-HBA below 2%, one has to work at a temperature of above at least 165° C. during the introduction of the carbon dioxide.

Finally, when the data in the comparative Examples and the Examples of the invention are reviewed it is apparent that, whereas the presently employed commercial processes for the preparation of salicylic acids result in the formation of at least about 10% non-salicylic acids, the practice of the present invention reduces non-salicylic acid formation to less than about 1%.

It will be further understood that the process described and illustrated above is obviously subject to variations and modifications without departing from the broader aspects of this invention.

What is claimed is:

1. A process for preparing sodium salicylate which comprises reacting phenol with an aqueous solution of sodium hydroxide in a reaction zone to form sodium phenolate; heating the resulting reaction product mixture at elevated temperatures, which are raised to above about 175° C., to remove water therefrom; introducing carbon dioxide into the reaction zone while the thus produced sodium phenolate is maintained at an elevated temperature above about 175° C., and producing sodium salicylate directly in a single step by reaction between the sodium phenolate and carbon dioxide at said elevated temperatures.

2. The process of claim 1 wherein said reaction temperature and the temperature at which the carbon dioxide is introduced is within the range of about 180° to 220° C.

3. The process of claim 1 wherein said reaction zone is a mixer and kneader device comprising counteracting blades to ensure thorough mixing of the phenol, sodium hydroxide, sodium phenolate, and carbon dioxide reactants throughout the process.

4. In a process for the production of salicylic acid comprising sequentially reacting phenol with an aqueous solution of sodium hydroxide in a reaction zone to form sodium phenolate, contacting carbon dioxide with said sodium phenolate to form sodium salicylate, and then acidifying said sodium salicylate to form salicylic acid; the improvement which comprises contacting the carbon dioxide with the sodium phenolate at a reaction temperature of above about 175° C. to reduce substantially the formation of by-product sodium salts of non-salicylic acids.

5. In the process of claim 4 wherein said reaction temperature and the temperature at which the carbon dioxide contacts the sodium phenolate is within the range of about 180° to 220° C.

6. In the process of claim 4 wherein said reaction zone is a mixer and kneader device comprising counteracting blades to ensure thorough mixing of the phenol, sodium hydroxide, sodium phenolate, and carbon dioxide reactants throughout the process.

* * * * *